United States Patent [19]

Swendson et al.

[11] Patent Number: 4,651,751

[45] Date of Patent: Mar. 24, 1987

[54] GUIDING CATHETER AND METHOD OF USE

[75] Inventors: David L. Swendson, Garden Grove; Edward E. Elson, Anaheim; Clement Lieber, Yorba Linda; Michael D. Rold, Costa Mesa, all of Calif.

[73] Assignee: American Hospital Supply Corporation, Deerfield, Ill.

[21] Appl. No.: 658,111

[22] Filed: Oct. 5, 1984

Related U.S. Application Data

[63] Continuation-in-part of Ser. No. 434,318, Oct. 14, 1982.

[51] Int. Cl.⁴ .............................................. A61N 1/04
[52] U.S. Cl. ................................... 128/786; 128/419 P
[58] Field of Search ................ 604/96, 280, 281, 282; 128/772, 784, 786, 419 P

[56] References Cited

U.S. PATENT DOCUMENTS

| | | | |
|---|---|---|---|
| 1,060,665 | 5/1913 | Bell | 604/281 |
| 2,437,542 | 3/1948 | Krippendorf | 604/282 |
| 3,687,142 | 8/1972 | Lebinzohn | 604/280 |
| 4,328,806 | 5/1982 | Cooper | 128/786 |
| 4,332,259 | 6/1982 | McCerkle, Jr. | 128/786 |

*Primary Examiner*—William E. Kamm
*Attorney, Agent, or Firm*—Gordon L. Peterson

[57] ABSTRACT

A guiding catheter adapted to be passed through the right side of the heart into the pulmonary artery and comprising a catheter body having at least first and second lumens extending longitudinally in the catheter body and a port extending from the first lumen to the exterior of the catheter body. The port is between the ends of the catheter and is in the right heart when the catheter is in use. An elongated stiffening element is locked within the second lumen and extends from a location on the proximal side of the port to a location on the distal side of the port. The stiffening element is flexible, but it is sufficiently stiff to cause the catheter to be gently curved along the stiffening element without forming a kink when the catheter is in use. The first lumen is adapted to have an inner catheter passed through it and out of the port into the right heart.

27 Claims, 16 Drawing Figures

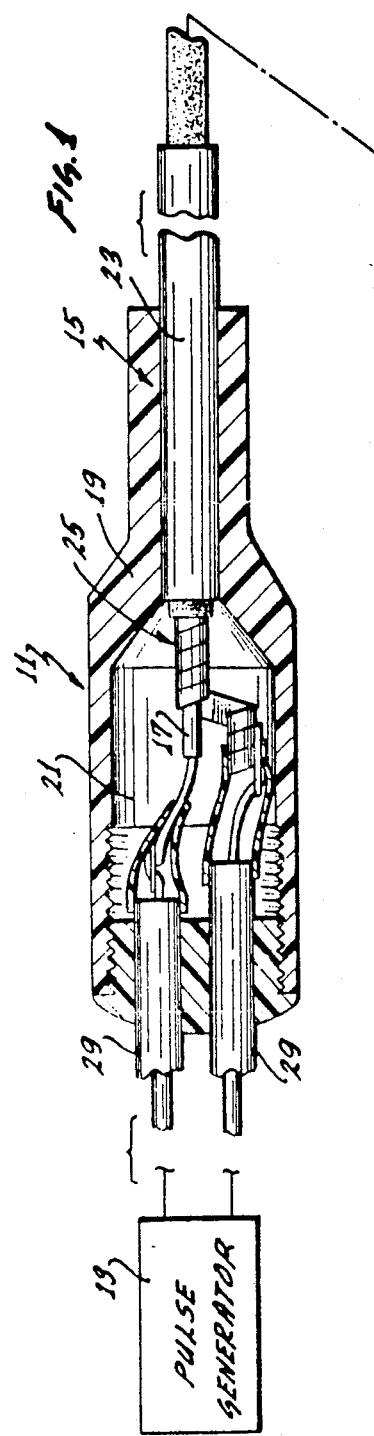
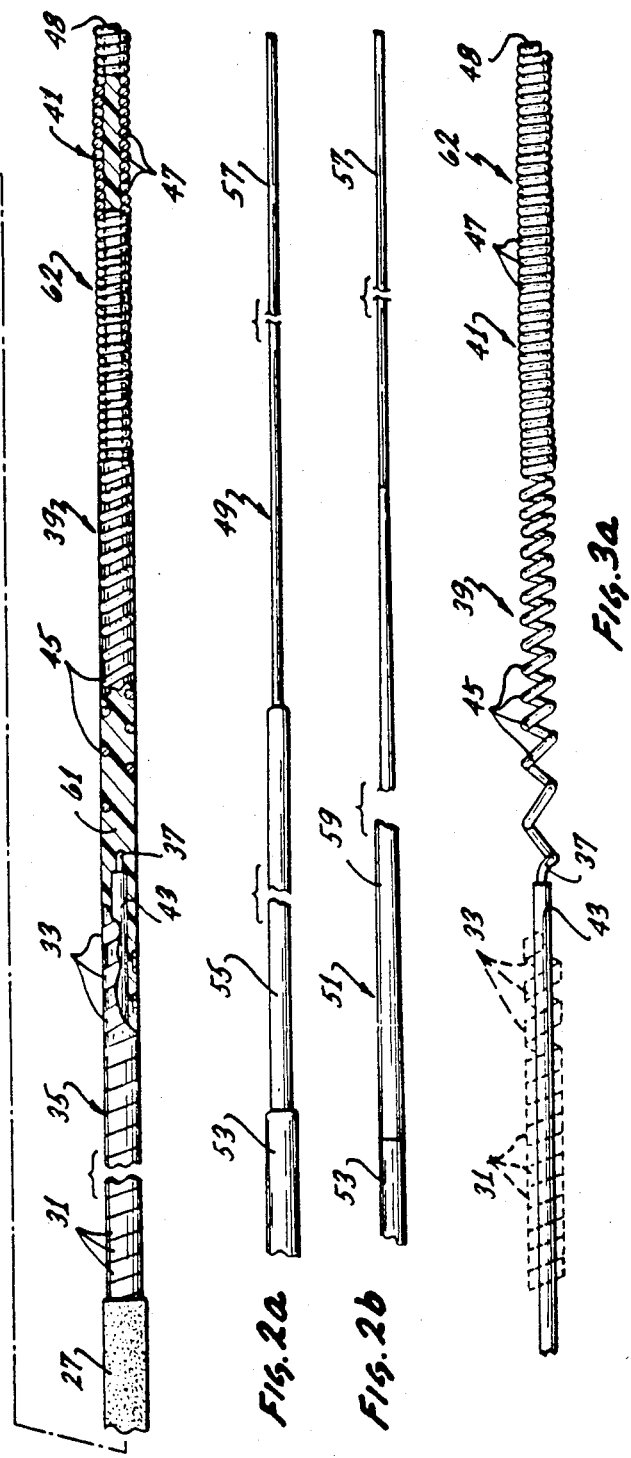

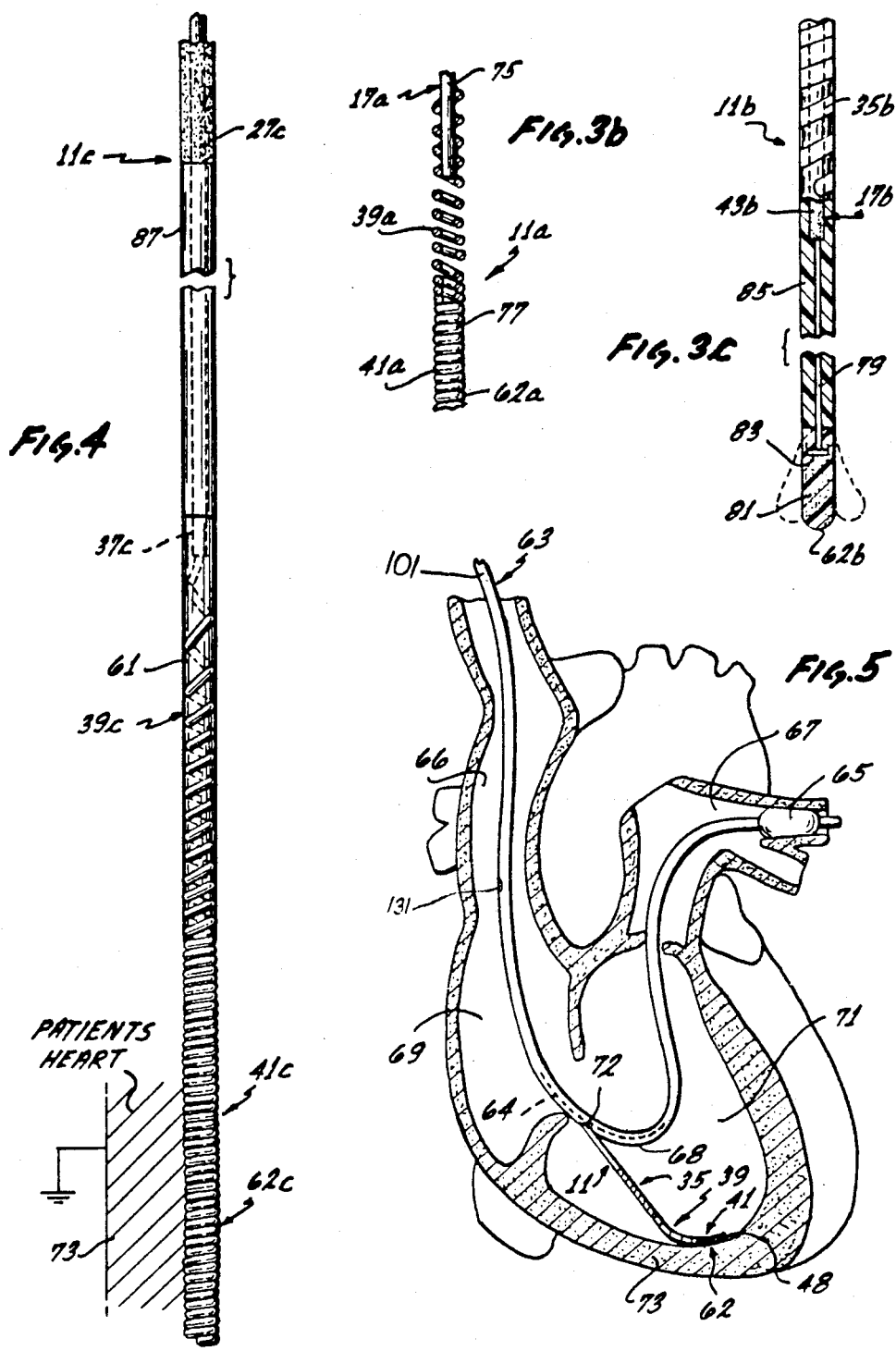

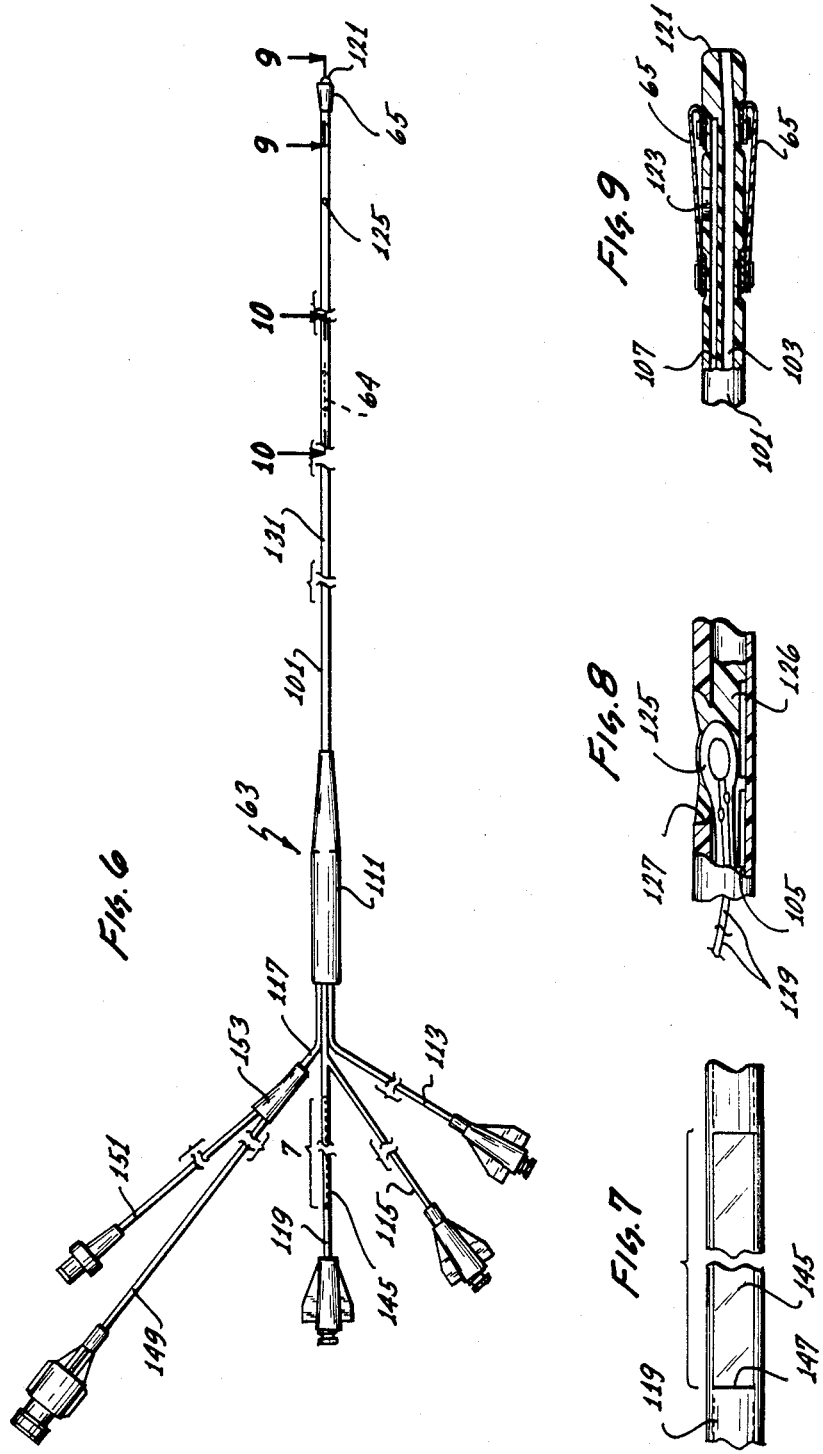

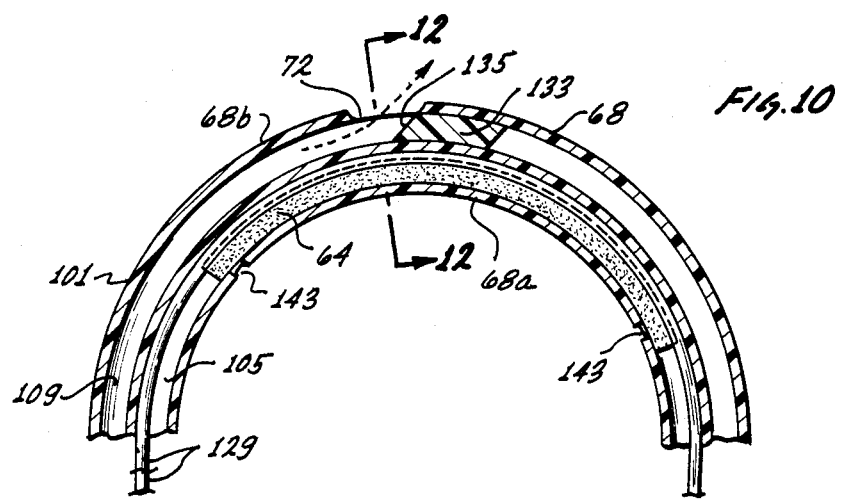
Fig. 10
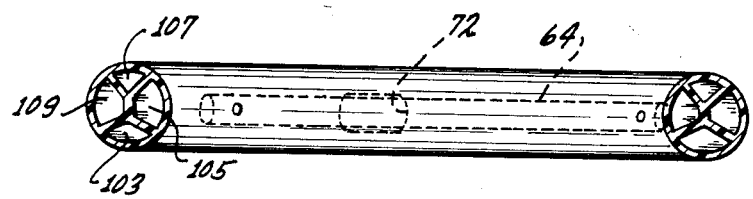
Fig. 11
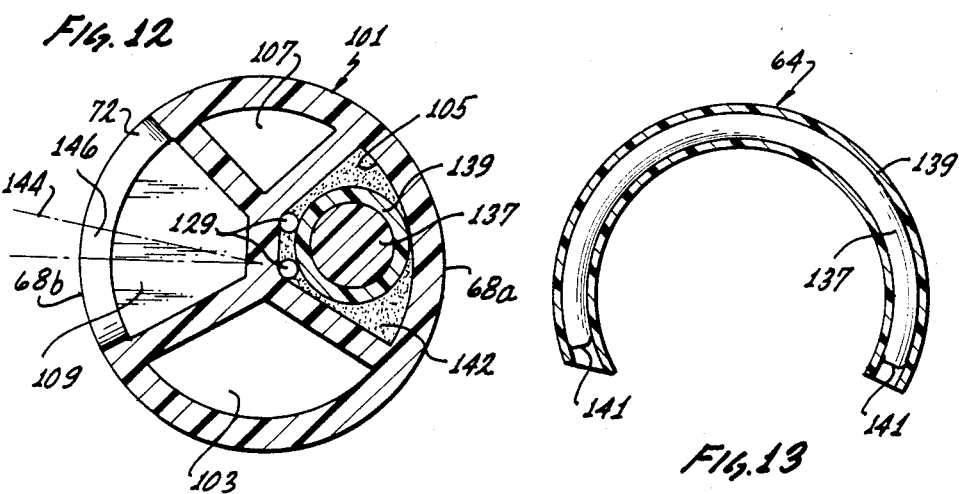
Fig. 12
Fig. 13

GUIDING CATHETER AND METHOD OF USE

This application is a continuation-in-part of application Ser. No. 434,318 filed on Oct. 14, 1982, and entitled Flexible Tip Cardiac Pacing Catheter.

BACKGROUND OF THE INVENTION

A pacing catheter and a pulse generator are used to electrically stimulate or pace the heart. To accomplish this, the catheter is inserted through a vein into the heart. Typically, the catheter is inserted into the right ventricle. The catheter may be either unipolar, i.e., have one electrode, or bipolar, i.e., have two electrodes. In either event, the distal electrode of the catheter must be brought into contact with the heart wall in order that pulses of electrical energy can be transmitted from the pulse generator through the catheter to the heart. Pacing of the heart in this fashion is often temporary and may be required, for example, in surgery following a myocardial infarction.

One problem with pacing catheters is that the insertion of the catheter into the heart and into engagement with the heart wall creates a risk of penetration of the heart wall by the catheter. The risk of penetration cannot be avoided by making the catheter uniformly flimsy because the catheter must have enough stiffness to be inserted into the heart. In addition, the catheter must have some resilience so that it can maintain the electrodes in substantially continuous contact with the heart wall in the presence of factors such as the beating of the heart and patient movement, which tend to interrupt engagement between the electrodes and the heart wall.

It is known to provide a flexible tail on a heart stimulation catheter and to space the electrodes proximally from the tail as shown in Harmjanz U.S. Pat. No. 3,664,347. In this construction, the tail must be in an artery of the lungs and neither of the electrodes is at or near the distal end of the catheter.

One way to insert a cardiac pacing catheter or other inner catheter is to advance it through the lumen of a pulmonary artery guiding catheter. To accomplish this, the guiding catheter must first be inserted through a vein and the right heart to the pulmonary artery, and this requires that the guiding catheter be formed into a curve in the right ventricle. The guiding catheter has a port within or adjacent the curve through which the pacing catheter can extend. One problem with this composite guiding catheterpacing catheter system is that the guiding catheter tends to form a sharp reverse bend or kink immediately distally of the port, and this is undesirable in that the kink can close off the lumens in the guiding catheter.

The guiding catheter is of necessity flexible, long and of very small diameter. It is inherently difficult to control the orientation of the port in a device of this type because the port tends to rotate about the long axis of the catheter. Proper control of the angular orientation of the port is important because port orientation materially influences the location of the pacing catheter in the heart.

SUMMARY OF THE INVENTION

This invention overcomes the problems noted above that are associated with guiding catheters. More specifically, this invention provides a guiding catheter which readily forms into a gentle bend or curve in the heart and does not kink when used with a pacing catheter.

One reason that a composite catheter system tends to kink is that the catheter system proximal to the port out of which the pacing catheter emerges is relatively stiff, and the guiding catheter distal to the port is relatively flexible. This abrupt change in stiffness at the port tends to cause kinking of the guiding catheter.

With this invention, a stiffening element, such as an elongated polymeric or metallic rod or wire, is permanently fixed, as by bonding, within the guiding catheter. The stiffening element begins proximal to the port and extends to a location distal to the port so that the region through the port and distally thereof is stiffened. The degree of stiffening is sufficent to permit the guiding catheter to form into the desired gentle curve without kinking. Preferably, the stiffening element terminates no farther distally than the right ventricle and no farther proximally than the superior vena cava, when the catheter system is used for pacing the right ventricle, the stiffening element preferably terminates at its opposite ends in the right atrium and the right ventricle.

The stiffening element also materially reduces the tendency of the guiding catheter to twist so as to harmfully disorient the port in a plane taken radially of the catheter. In addition, the stiffening element prevents the catheter port from rotating about the longitudinal axis of the catheter during sterilization and packaging of the catheter. Accordingly, the pacing catheter can be directed to the desired location in the heart with much greater accuracy.

Stiffening elements for catheters are known, and one catheter having a stiffening element is shown in Blake et al U.S. Pat. No. 3,995,623. However, the Blake et al stiffening element is provided for facilitating the formation of a sharp bend or kink in the catheter, and there is no cooperation between it and a port used for delivery of an inner catheter to the heart.

The orientation of the port in a radial plane is important in guiding the inner catheter to the desired location. For a pacing catheter, the center of the port should be generally on the outside of the curve, and preferably, the center of the port as viewed in a radial plane forms an angle of no more than about 30 degrees with a radial reference line which bisects the portion of the curve which faces outside.

To facilitate the passage of the inner catheter through the port into the right heart, the lumen containing the port is preferably at least partially closed. Such closing means preferably includes a sloping surface facing proximally in the lumen to guide the inner catheter out through the port. To permit the port to be accurately located when the catheter is within the body, the closing means can advantageously include a radiopaque plug.

In order to form the desired gentle bend, the stiffening element is preferably of substantially constant thickness throughout nearly its full length. However, to blend the relatively stiff stiffening element into the relatively flexible body of the catheter, axially short end portions of the stiffening element can advantageously have a lesser stiffness than a central section intermediate such end portions.

So that the stiffening element can provide the desired gentle curve, it is preferably preformed into a curve. In a preferred construction, the curve is circular and extends for over 180 degrees. The stiffening element is permanently fixed, as by bonding, within a lumen of the catheter body so that the stiffening element is held against rotation in the lumen. With this construction, the stiffening element can act to resist torsional displacement of the port during sterilization and use of the guiding catheter.

The guiding catheter of this invention is particularly adapted for use with a pacing catheter, although it may be used with various inner catheters of different constructions. As used herein, the terms pacing catheter and inner catheter include both catheters and probes which may be passed through an outer or guiding catheter.

The invention, together with additional features and advantages thereof, may best be understood by reference to the following description taken in connection with the accompanying illustrative drawing.

BRIEF DESCRIPTION OF THE DRAWING

FIG. 1 is a side elevational view partially in section of a bipolar catheter constructed in accordance with the teachings of this invention coupled to a pulse generator.

FIGS. 2a and 2b are fragmentary side elevational views showing two different forms of wire which can be used for the conductor.

FIGS. 3a, 3b and 3c are side elevational views of three forms of bipolar flexible tip catheters of this invention, respectively. The elastomeric material within the coils is not shown in FIGS. 3a and 3b.

FIG. 4 is a front elevational view of a unipolar catheter constructed in accordance with the teachings of this invention.

FIG. 5 is a sectional view through a human heart showing one way in which the catheter of this invention can be used.

FIG. 6 is an elevational view of a guiding catheter laid out flat and constructed in accordance with the teachings of this invention.

FIG. 7 is an enlarged, fragmentary elevational view of the proximal portion of the catheter which is designated by the bracket 7 of FIG. 6.

FIG. 8 is a fragmentary, sectional view of the catheter illustrating the thermistor and the adjacent region of the catheter.

FIG. 9 is an enlarged, sectional view taken generally along line 9—9 of FIG. 6.

FIG. 10 is an enlarged, fragmentary sectional view taken generally along line 10—10 of FIG. 6 with the portions shown in FIG. 10 being in the generally arcuate configuration which it assumes in packaging and when unstressed.

FIG. 11 is an elevational view of the construction shown in FIG. 10.

FIG. 12 is an enlarged, sectional view taken generally along line 12—12 of FIG. 10.

FIG. 13 is a plan view of one form of stiffening element.

DESCRIPTION OF THE PREFERRED EMBODIMENTS

FIG. 1 shows a bipolar pacing catheter 11 which is one form of inner or pacing catheter that can be used with a guiding catheter 63 (FIGS. 5 and 6) of this invention. The pacing catheter 11 is electrically coupled to a pulse generator 13 and generally comprises a body 15 and an elongated inner conductor 17.

The body 15 includes a backshell 19 having an interior chamber 21, a tube 23 received within one end of the backshell 19, an outer conductor 25 and a flexible outer cover 27 of a suitable material, such as polytetrafluoroethylene. The conductors 17 and 25 are suitably coupled within the chamber 21 to leads 29 leading to the pulse generator 13. The chamber 21 may contain a suitable potting compound (not shown) if desired.

In the embodiment illustrated, the outer conductor 25 is in the form of a flat wire, i.e., a wire of nearly rectangular cross section, wound into a series of contiguous coils 31 which extend from the chamber 21 to a location distally of the cover 27 and axially spaced coils 33 located distally of the contiguous coils 31. The cover 27 terminates proximally of the distal end of the conductor 25, and the exposed portion of this conductor forms an electrode 35.

The inner conductor 17 is also in the form of an elongated wire having a first section 37 extending from the chamber 21 axially through the body 15, a transition section 39 and a distal section 41 with the portion of the inner conductor 17 which is outside of said body being the distal end portion of the inner conductor. As best shown in FIG. 3a the first section 37 is straight and is covered by insulation 43. The transition section 39 comprises a plurality of coils 45 which is spaced apart axially, with the axial spacing between adjacent coils progressively reducing as the transition section extends distally. This progressive reduction in spacing is preferred but not essential. The distal section 41 comprises a plurality of contiguous coils 47 and terminates at a distal end 48 of the catheter 11. These coils could be tightly or loosely wound to further control flexibility.

The inner conductor 17 may be formed, for example, of a wire 49 (FIG. 2a) or of a wire 51 (FIG. 2b). The wire 49 has a cylindrical section 53 of relatively large diameter which can be used to form the first section 37 and cylindrical sections 55 and 57 which can be used to form the transition section 39 and the distal section 41, respectively. Each of the sections 55 and 57 is of lesser diameter than the cylindrical section immediately proximally thereof.

The wire 51 also has a cylindrical section 53 from which the first section 37 can be formed. However, in lieu of the cylindrical section 55, the wire 53 has a conical section 59 which is of progressively reducing diameter as it extends distally and from which the transition section 39 can be constructed. The wire 53 also has a cylindrical section 57 from which the distal section 41 can be constructed. The wires 49 and 51 can be constructed of various suitable materials, such as stainless steel. The wires 49 and 51 can be formed of multiple sections which are suitably joined together as by soldering or welding but, preferably, each of these wires is integral. In this latter event, the wires 49 and 51 can be tapered by electropolishing or centerless grinding.

With the construction described above, the first section 37 is less flexible than the transition section 39 and the transition section 39 is less flexible than the distal section 41. Also, the first section 37 is reinforced by the body 15. Moreover, the flexibility of the transition section 39 increases as the transition section extends distally. The relative stiffness of the first section 37 is obtained by leaving the first section 37 uncoiled and constructing it of larger diameter wire. The transition section 39 is more flexible than the first section 37 because it is coiled and constructed of smaller diameter wire. The flexibility of the transition section 39 increases because the axial spacing between the coils 45 decreases as the transition section extends distally and because the conical section 59 of the wire is of progressively decreasing diameter. The distal section 41 is more flexible than the transition section 39 because the coils 47 are contiguous and because wire of minimum diameter is used to construct it. The distal section 41 is flexible and resilient all the way to the distal end 48.

In the embodiment of FIGS. 1-3, a non-conductive elastomer 61 fills the central space within the coils 47, 45 and 33. The elastomer 61 helps insulate the conductors 17 and 25 from each other. In the embodiment illustrated, the elastomer 61 terminates, along with the distal section 41, at the distal end 48. In this embodiment, the presence of the elastomer 61 does not alter the above-described relative stiffness relationships of the sections 37, 39 and 41. The elastomer 61 fills the spaces between the coils 45 and the coils 33, and in addition, encases the coils 45 of the transition section 39 so that only the coils 47 are exposed to define an electrode 62. In this embodiment, the distal section 41 forms the electrode 62. If the elastomer 61 is eliminated, then it is preferred to encase the coils 45 of the transition section 39 in a suitable insulation jacket.

FIG. 3b shows a catheter 11a which is identical in all respects not shown or described herein to the catheter 11. Portions of the catheter 11a corresponding to portions of the catheter 11 are designated by corresponding reference numerals followed by the letter "a."

The only difference between the catheters 11 and 11a is that the inner conductor 17a of the catheter 11a is provided in two parts, i.e., a straight segment 75 and a coiled segment 77 appropriately joined together as by solder or welding. For this purpose, the distal end of the straight segment 75 is inserted within a few of the proximal coils of the coiled segment 77. The straight segment 75 defines the first section 37a and the coiled segment 77 defines the transition section 39a and the distal section 41a, i.e., the electrode 62a.

FIG. 3c shows a catheter 11b which is identical to the catheter 11 in all respects not shown or described herein. Portions of the catheter 11b corresponding to portions of the catheter 11 are designated by corresponding reference numerals followed by the letter "b."

In the catheter 11b, the inner conductor 17b comprises a segment 79 and a body 81 of soft, flexible resilient, conductive elastomeric material attached to the distal end of the segment 79. The segment 79 may be a wire or cable. The distal portion of the segment 79 projects beyond the insulation 43b and terminates in a head 83 of enlarged cross-sectional area.

The segment 79 between the body 81 and the electrode 35b is encased in a jacket 85 of soft, flexible, resilient plastic material, which is a nonconductor. This portion of the segment 79 and the jacket 85 form a transition section 39b of a stiffness intermediate the stiffness of the body 81 and the region of the catheter 11b proximally of such portion of the segment 79. The segment 79 projects only a short distance into the body 81, and hence, the body 81 is the most flexible part of the inner conductor 17b. The jacket 85 may extend into the coils defining the electrode 35b.

The body 81 of elastomeric material may be, for example, molded around the distal tip of the segment 79 so that the head 83 is embedded within the body 81. This tightly retains the body 81 of elastomeric material against the distal end of the jacket 85. If desired, the body 81 may be adhered or bonded to the jacket 85. The body 81 forms the distal electrode 62b.

FIG. 4 shows a unipolar catheter 11c which is identical in all respects not shown or described herein to the bipolar catheter 11. The only difference between the catheters 11 and 11c is that the outer conductor 25 is replaced with a flexible tube 87 of a suitable biocompatible plastic material. Portions of the catheter 11c corresponding to portions of the catheter 11 are designated by corresponding reference numerals followed by the letter "c." As shown schematically in FIG. 4, with the unipolar catheter 11c, the circuit is completed through a wall 73 of the right ventricle to ground, and to accomplish this, the patient is appropriately grounded.

FIG. 5 shows how the guiding catheter 63 of this invention can be used to guide and direct an inner catheter, such as any of the inner catheters shown in FIGS. 1-4. The guiding catheter 63 is described generally with reference to FIG. 5 and, more specifically, with reference to FIGS. 6-13. Considering first the general description of FIG. 5, the guiding catheter 63 has a catheter body 101 which may be inserted into the heart through a vein using conventional techniques. Following such insertion, a balloon 65 adjacent the distal end of the guiding catheter 63 is lodged in the pulmonary artery 67. As shown in FIG. 5, the guiding catheter 63 extends through the superior vena cava 66 and is formed into a curve 68 of about 180 degrees as it extends through the right atrium 69 and the right ventricle 71. The guiding catheter 63 has a port 72 leading from one of its lumens into the right ventricle 71.

In the embodiment illustrated, the stiffening element 64 is in the form of an elongated, flexible, resilient rod or wire of metal, elastomer or plastic bonded into the guiding catheter 63 outside of the lumen with which the port 72 communicates. In the preferred construction illustrated, the stiffening element 64 extends from a location in the right atrium 69 proximally of the port 72 continuously to a location in the right ventricle 71 located distally of the port 72. Thus, regions of the guiding catheter adjacent the port 72 on the opposite sides of the port 72 are stiffened, and such stiffening is controlled and sufficient to cause the catheter 63 to form the relatively gentle curve 68 in the right heart without kinking as the catheter extends through the right heart to the pulmonary artery 67.

With the guiding catheter 63 positioned in the right heart as shown in FIG. 5, the catheter 11 can be inserted through a lumen of the guiding catheter 63 and out the port 72. As the catheter 11 continues its advancing movement, the electrode 62 contacts the wall 73 of the right ventricle and bends over or deflects along the wall due to the resilience of the distal section 41 all the way to the distal end 48. This causes the electrode 62 and the transition section 39 to resiliently flex and causes the electrode to lie against the wall 73 without penetrating the wall. A circuit can then be completed from the electrode 62 through the heart wall 73 and body fluids in the heart to the electrode 35. The flexibility of the catheter 11, and in particular, of the conductors 17 and 25 at, and distally of the distal electrode 35, maintains the distal electrode 62 in continuous engagement with the wall 73. The inner catheter 11 is flexible throughout its length. However, the resilience and flexibility of the catheter are carefully controlled primarily at the sections 39 and 41 to provide insufficient column strength to penetrate the heart wall 73 and sufficient resilience to maintain contact between the distal electrode 62 and the heart wall.

FIGS. 6-13 show a preferred form of the guiding catheter 63 in greater detail. The catheter body 101 in the embodiment illustrated, has a through lumen 103 (Fig. 12), a stiffener lumen 105, a balloon inflation lumen 107 and a guiding lumen 109. The catheter body 101 terminates proximally in a hub 111, and each of the lumens 103, 105, 107 and 109 terminate proximally at the proximal end of the catheter body. Connector tubes 113, 115, 117 and 119 are mounted within the proximal ends of the lumens 103, 105, 107 and 109, respectively, in a conventional manner.

The through lumen 103 extends completely through the catheter body 101 to a distal end 121 (FIG. 9), and the balloon inflation lumen 107 extends to a location adjacent the distal end 121 where it communicates with the interior of the balloon 65 via a port 123. The balloon 65 is retained on the catheter body 101 in a conventional manner.

A thermistor 125 (FIGS. 6 and 8) is suitably mounted in the stiffener lumen 105 as by potting 126 and is exposed by a port 127 in the stiffener lumen. Thermistor wires 129 extend proximally from the thermistor 125 through the stiffener lumen 105 to a location adjacent an injectate port 131 (FIG. 6) in the stiffener lumen, and at this location, the thermistor wires 129 cross over into the balloon inflation lumen 107. The cross over of the thermistor wires 129 between lumens may be accomplished as shown in Lieber et al U.S. Pat. No. 4,329,993. The thermistor wires 129 extend from the cross-over location to the connector tube 117 in the balloon inflation lumen 107.

The guiding lumen 109 extends to the port 72 (FIG. 10), and the lumen is closed just distally of the port 72 by a plug 133 of suitable radiopaque material, such as a mixture of polyvinylchloride and tantalum. The plug 133 has a sloping surface 135 which is inclined distally as it extends outwardly toward the port 72 to facilitate the passage of the inner catheter 11 through the port 72 into the right heart. To further facilitate exit of the inner catheter 11, the port 72 is preferably elongated in a direction axially of the catheter body 101.

The stiffening element 64 may be of various different constructions, and in the embodiment illustrated in FIG. 13, it includes a nylon core or rod 137 encased within a tube or jacket 139 of a suitable plastic, such as PVC. The rod 137 is preformed into an arc and, preferably, is preformed into a circular arc. Although the extent of the circular arc can vary, preferably, it extends for over 180 degrees, and about 240 degrees is considered generally optimum. The preforming of the nylon rod 137 can be carried out at elevated temperatures. Thereafter, the tube 139 is shrunk over the rod. The rod 137 has opposite ends 141, and between such ends, the stiffening element 64 is of essentially constant cross section such that the stiffness of this relatively large central section is substantially constant. To provide the stiffening element with end portions of somewhat lesser stiffness than the central section, the tube 139 extends for a short distance beyond the ends 141. For example, in a case where the stiffening element 64 is about four inches in length, the tube 139 may project about 0.1 to about 0.2 inch beyond each of the ends 141.

The stiffening element 64 is inserted through the stiffener lumen 105 to the desired location and strongly bonded in the lumen 105 with a bonding agent 142 so that it is held against rotation in the lumen. The bonding agent 142, which may be, for example, vinyl or urethane, can be injected through apertures 143 (FIG. 10) into the lumen 105, and the bonding agent 142 preferably fills the remaining space in the lumen for the full length of the stiffening element 64. The bonding agent 142 also closes the apertures 143.

As shown in FIG. 10, the stiffening element 64 extends farther proximally of the port 72 than distally. By way of example, the stiffening element may extend about 2.5 inches distally from the center of the port 72 and about 1.5 inches proximally from the center of the port 72. The stiffening element 64 extends slightly beyond both of the apertures 143, and the catheter body 101 straightens the stiffening element 64 somewhat into the gentle curve 68 as shown by way of example in FIG. 10. As shown in the preferred embodiment of FIG. 6, the stiffening element 64 lies proximally of the balloon 65, and the thermistor 125 is between the stiffening element and the balloon.

The stiffener lumen 105 need not be diametrically opposite the guiding lumen 109. For example, the stiffener lumen 105 may occupy the position of any of the lumens 103, 105 or 107.

The curved stiffening element 64 generally forms the catheter body 101 into the curve 68 (FIGS. 5 and 10). The curve 68 has an inside 68a and an outside 68b, and the port 72 is on the outside 68b of the curve 68 so that the inner catheter 11 will be properly located in the heart. In this embodiment, a radial line 144 through the center 146 (FIG. 12) of the port 72 forms a small angle of about 10 degrees with a radial reference line 148 which bisects the portion of the curve 68 which faces the outside 68b. Preferably, this angle is no greater than about 30 degrees. With this arrangement, the inner catheter 11 exits generally tangent to the curve 68.

The connector tube 119 has a transparent section 145 (FIGS. 6 and 7), and the distance between the center of the port 72 and a proximal edge 47 of the transparent section is accurately controlled. In use of the guiding catheter 63, the inner catheter 11 is advanced through the connector tube 119 and the guiding lumen 109 to the port 72 as described in connection with FIG. 5. The inner catheter 11 has a suitable marker which appears at the proximal edge 147 when the distal end 48 is at the port 72. In this manner, the physician knows when the inner catheter 11 is about to exit from the lumen 109 through the port 72.

The connector tube 113 and the through lumen 103 can be used in a conventional manner for various purposes, such as blood pressure monitoring and blood sampling, and the connector tube 115 and the stiffener lumen 105 may be used, for example, to inject an injectate through the injectate port 131 into the superior vena cava 66 or the right atrium 69 for purposes, such as cardiac output measurements by means of thermodilution. The connector tube 117 is coupled to branch tubes 149 and 151 by a conventional connector 153, and the branch tubes 149 and 151 may be used to carry the thermistor wires 129 and for carrying a fluid for inflation and deflation of the balloon 65, respectively.

Although exemplary embodiments of the invention have been shown and described, many changes, modifications and substitutions may be made by one having ordinary skill in the art without necessarily departing from the spirit and scope of this invention.

We claim:

1. A guiding catheter adapted to be passed through the right side of the heart into the pulmonary artery, said guiding catheter comprising:

an elongated catheter body having proximal and distal ends, at least one lumen extending longitudinally in the body and a port extending from the lumen to the exterior of the catheter body, said port being in the right ventricle when the catheter extends through the right ventricle into the pulmonary artery for passing an inner catheter from said lumen through said port into the right ventricle; and an elongated stiffening element permanently fixed within the catheter body and extending from a location on the proximal side of said port to a location on the distal side of the port, said stiffening element being curved, flexible and sufficiently stiff to cause the catheter to form a gentle curve without forming a kink when the catheter extends through the right ventricle to the pulmonary artery.

2. A guiding catheter as defined in claim 1 wherein said stiffening element extends no farther proximally than the superior vena cava when the guiding catheter extends through the right heart to the pulmonary artery and no farther distally than the right ventricle when the guiding catheter extends through the right heart to the pulmonary artery.

3. A guiding catheter as defined in claim 1 wherein said elongated stiffening element terminates in the right atrium and the right ventricle when the catheter extends through the right heart to the pulmonary artery.

4. A guiding catheter as defined in claim 1 including means for at least partially closing said one lumen adjacent said port without closing said port to facilitate the passage of the inner catheter through the port into the right heart and said closing means includes a radiopaque plug.

5. A guiding catheter as defined in claim 4 wherein said closing means includes a sloping surface facing proximally in said one lumen to facilitate the passage of the inner catheter through the port into the right heart.

6. A guiding catheter as defined in claim 1 wherein said stiffening element has a central section of substantially constant stiffness and end portions of lesser stiffness than said central section.

7. A guiding catheter as defined in claim 1 wherein said catheter body has a second lumen therein and said stiffening element is preformed into a curve and bonded in said second lumen so that the stiffening element is held against rotation in the second lumen.

8. A guiding catheter as defined in claim 7 wherein said stiffening element in an unstressed condition forms a generally circular arc which extends for over 180 degrees.

9. A guiding catheter as defined in claim 1 wherein said stiffening element extends farther distally of said port than proximally of said port.

10. A guiding catheter as defined in claim 1 wherein the center of said port is generally on the outside of said curve.

11. A guiding catheter as defined in claim 1 wherein a radial line through the center of the port as viewed in a radial plane forms an angle of no more than about 30 degrees with a radial reference line which bisects the portion of the curve which faces outside.

12. A guiding catheter adapted to be passed through the right side of the heart into the pulmonary artery, said guiding catheter comprising:

an elongated catheter body having proximal and distal ends, at least one lumen extending longitudinally in the body and a port extending from the lumen to the exterior of the catheter body, said port being in the right ventricle when the catheter extends through the right heart into the pulmonary artery for passing an inner catheter from said lumen through said port into the right ventricle;

an elongated stiffening element permanently fixed within the catheter body and held against rotation in the catheter body, said stiffening element extending from a location on the proximal side of said port to a location on the distal side of said port and being flexible, a region of said catheter body and stiffening element being curved and said port being on said curved region, said stiffening element resisting torsional displacement of the port.

13. A guiding catheter as defined in claim 12 wherein said stiffening element extends farther distally of said port than proximally of said port.

14. A guiding catheter as defined in claim 12 wherein the center of said port is generally on the outside of said curve.

15. A guiding catheter as defined in claim 14 wherein a radial line through the center of the port as viewed in a radial plane forms an angle of no more than about 30 degrees with a radial reference line which bisects the portion of the curve which faces outside.

16. A guiding catheter as defined in claim 12 including a balloon on said catheter body distally of the port, said catheter body having balloon inflation lumen means communicating with the balloon for use in inflating the balloon and said first location being distally of said proximal end and said second location being proximally of said balloon.

17. A guiding catheter as defined in claim 16 wherein said catheter body has an injectate port located proximally of said first location.

18. A guiding catheter as defined in claim 16 wherein said stiffening element extends farther distally of said port than proximally of said port.

19. A guiding catheter as defined in claim 12 wherein said locations are spaced substantially from said ends of the catheter body.

20. A guiding catheter adapted to be passed through the right side of the heart into the pulmonary artery, said guiding catheter comprising:

an elongated catheter body having proximal and distal ends, at least one lumen extending longitudinally in the body and a port extending from the lumen to the exterior of the catheter body, said port being in the right ventricle when the catheter extends through the right heart into the pulmonary artery for passing an inner catheter from said lumen through said port into the right ventricle;

an elongated stiffening element permanently fixed within the catheter body and extending from a first location on the proximal side of said port to a second location on the distal side of said port, said stiffening element being flexible;

a balloon on said catheter body distally of the port, said catheter body having balloon inflation lumen means communicating with the balloon for use in inflating the balloon; and said first location being distally of said proximal end and said second location being proximally of said balloon whereby the stiffening element is shorter than the catheter body.

21. A guiding catheter as defined in claim 20 including a thermistor carried by the catheter body intermediate said second location and said balloon.

22. A guiding catheter as defined in claim 20 wherein said catheter body has an injectate port located proximally of said first location.

23. A guiding catheter as defined in claim 22 wherein said catheter body has a stiffener lumen and said stiffener element is in said stiffener lumen and said injectate port leads from the stiffener lumen.

24. A guiding catheter as defined in claim 20 wherein said stiffening element extends farther distally of said port than proximally of said port.

25. A catheter system for pacing the heart comprising:

a guiding catheter which can be passed through the right ventricle and into the pulmonary artery, said guiding catheter having proximal and distal ends, at least one lumen extending longitudinally in the guiding catheter and a port extending from the lumen to the exterior of the guiding catheter, said port being exposed in the right ventricle when the guiding catheter extends through the right ventricle into the pulmonary artery;

an elongated stiffening element permanently fixed within the catheter and extending from a location on the proximal side of said port to a location on the distal side of said port, said stiffening element being curved, flexible and sufficiently stiff to cause the guiding catheter to be gently curved without forming a kink when the guiding catheter extends through the right ventricle to the pulmonary artery;

a cardiac pacing catheter including at least one electrode; and said pacing catheter extending through said lumen and passing through said port.

26. A catheter system as defined in claim 25 wherein said stiffening element extends no farther proximally than the right atrium when the guiding catheter extends through the right heart into the pulmonary artery and no farther distally than the right ventricle when the guiding catheter extends through the right heart into the pulmonary artery.

27. A method of pacing the heart comprising:

providing a guiding catheter having proximal and distal ends, at least one lumen extending longitudinally in the guiding catheter, a port extending from the lumen to the exterior of the guiding catheter, and an elongated flexible stiffening element permanently fixed within the guiding catheter and extending from a location on the proximal side of said port to a location on the distal side of said port;

positioning the guiding catheter in a patient with the port being in the right ventricle, the distal end in the pulmonary artery and with the guiding catheter being formed into a curve without forming a kink in extending through the right ventricle to the pulmonary artery;

advancing a cardiac pacing catheter through the lumen out of the port and into contact with a wall of the heart; and pacing the heart with the pacing catheter.

* * * * *